US00PP22817P3

(12) United States Plant Patent
VanLaeken

(10) Patent No.: US PP22,817 P3
(45) Date of Patent: Jun. 26, 2012

(54) ***CLEMATIS* PLANT NAMED 'FESTIVAL'**

(50) Latin Name: ***Clematis* sp.**
Varietal Denomination: Festival

(76) Inventor: James P VanLaeken, Walworth, NY (US)

( * ) Notice: Subject to any disclaimer, the term of this patent is extended or adjusted under 35 U.S.C. 154(b) by 0 days.

(21) Appl. No.: 12/807,754

(22) Filed: Sep. 14, 2010

(65) Prior Publication Data

US 2012/0066805 P1 Mar. 15, 2012

(51) Int. Cl.
*A01H 5/00* (2006.01)

(52) U.S. Cl. ..... Plt./228

(58) Field of Classification Search ..... Plt./228
See application file for complete search history.

*Primary Examiner* — Susan McCormick Ewoldt

(57) ABSTRACT

A new variety of *clematis* plant named 'Festival'. The variety is characterized by it's dwarf growing habit and prolific very symmetrical bicolor blooms. The compact habit, high bud count, compact dark green foliage make this an excellent *clematis* for containers and small spaces.

3 Drawing Sheets

Botanical classification: *Clematis* sp.
Cultivar designation: 'Festival'.

BACKGROUND OF THE VARIETY

The present invention relates to a new and distinct variety of hybrid *clematis* plant known by the cultivar name 'Festival'.

The new variety was a chance seedling that was picked out of a group of seedlings growing in a controlled planting at my nursery, in Walworth N.Y. in 2003. This variety was picked out because of it's compact growth habit, prolific and symmetrical blooms. This variety was asexually propagated by soft wood cuttings in greenhouses in Walworth N.Y., and observed over the next six years. Asexual propagation by vegetative cuttings has shown that the propagules are identical to the original plant and all distinguished characteristics. The stability of the variety is evidenced by the distinguished characteristics remaining true to form from generation to generation.

SUMMARY OF THE INVENTION

Among the features which distinguish the new variety from other present available and known commercial *clematis* cultivars is it works well in a container due to it's compact growth and prolific blooming habits. The unique color, uniform size, and the abundance of blooms make this cultivar unique.

RELEVANT PRIOR ART

This new variety is similar to *Clematis* sp. 'Mrs. N. Thompson', a non patent *Clematis* variety. *Clematis* sp. 'Festival' has more overlapping tepals also the center stamens are more appealing and the growth habit is stronger.

BRIEF DESCRIPTION OF THE PHOTOGRAPH

The accompanying photographs illustrates the overall appearance of the new variety. The flowering and foliage colors as shown are, within the limitations of color photography, accurate and true reproductions of the actual colors of new variety.

Sheet one is a photographic front view of a close up of a typical *Clematis* sp. 'Festival'.

Sheet two is a view of the typical leaves, flower buds, and backside of flower.

Sheet three is a view typical form and growth habit of *Clematis* sp. 'Festival'.

BOTANICAL DESCRIPTION

The following information is based on a three year old plant grown in 50% shade in a five gallon container in a covered greenhouse with 60° F. ambient night temperatures and 75° F. ambient day temperatures in Walworth, N.Y. Color references are based on using the PANTONE® matching system.

I. Plant:

*A. Form.*—Upright climbing or spreading, no lateral branching was observed.

*B. Growth.*—Vigorous, vining. 1. Height: approximately 4 feet to 6 feet. 2. Diameter/Spread: approximately 1.5 feet to 2.5 feet.

*C. Foliage.*—Deciduous, compound-trifoliate, opposite. 1. Size, typical and observed: a. compound leaf length 3 to 4 inches, width 3 to 4 inches. b. individual leaflets length 1.5 to 2 inches, width 0.5 to 1 inch. c. leaflets per compound leaf: 3. 2. Quantity of leaves per stem: typically and observed: about 45. 3. Color: a. upper surface: dark green (PANTONE® #575U). b. lower surface: medium green (PANTONE® #7491U). 4. Shape: a. leaflets: the leaves are elliptical, margin is untoothed with pubescent edge, apex is pointed. 5. Texture: a. upperside: smooth and veined. b. underside: ribbed and pubescent on veins and edges. c. venation pattern: leaflets palmatic with green coloration on upper and lower. 6. Petiole: a. color: medium green (PANTONE® #582U). b. length, typical and observed: 1 to 1.5 inches. c. diameter, typical and observed: 1/16 inch. d. glabrous: no.

*D. Wood.*—1. New Shoots: a. color: light green (PANTONE® #583C) with a faint reddish black tint (PANTONE® #696C). b. bark: pubescent. c. internodes: cylindrical, approximately 2 to 3 inches in length and 1/16 inch in diameter. 2. Old Wood: a. color: medium to dark brown (PANTONE® #4635C). b. bark: smooth ⅛ inch in diameter. c. internodes: cylindrical, approximately 3 to 4 inches in length and ⅛ inch in diameter and pubescent.

*E. Hardiness.*—US Zones 4 through 8. 1. low temperature tolerance, typical and observed: −10° F. to 0° F. 2. high temperature tolerance, typical and observed: 90° F. to 110° F.; requires 6 to 8 weeks dormancy at 35° F. to 40° F. to remain vigorous.

*F. Disease.*—1. Subject to any disease that affects *clematis*. a. wilt. b. botrytis. c. powdery mildew.

*G. Pests.*—1. Subject to any pest that normally affect *clematis*. a. aphids. b. spider mites. c. slugs and snails.

II. Flower:

*A. Blooming habit.*—May and June on new and old growth based on climate in Rochester, N.Y. area.

*B. Bud.*—1. Size: typical and observed from about 1 to 1.75 inches in length and about ½ to 1 inch in diameter. 2. Form: ovate base with pointed tip. 3. Color: light green (PANTONE® #578C) with pinkish veins (PANTONE® #516C).

*C. Stem.*—1. Dimension, typical and observed: length 1 to 2 inches, diameter 1/16 inch. 2. Aspect: vertical. 3. Strength: erect. 4. Color: light green (PANTONE® #578C).

*D. Bloom.*—1. Size: typical and observed from about 3 to 5 inches in diameter with a depth of about ¾ inch. 2. Form: round shaped with 6 to 8 tepals of equal size overlapping. 3. Color upper surface: bluish purple (PANTONE® #2572C) with reddish bar (PANTONE® #225C). 4. Color of lower surface: outer edge is bluish purple (PANTONE®#2645U) middle is white with prominent veins. 5. Characteristics: born on 1.5 to 2 inch stems on new and old growth. 6. Quantity: 1 bloom per stem, 2 to 3 blooms per node from 2 or 3 to several hundred blooms per plant depending on the age and size of plant. 7. Lastingness: 3 to 6 days as a cut flower or 7 to 10 days on plant.

*E. Tepals.*—1. Form: elliptical shape, narrow at base rounding at mid section width 1 inches to 1.25 inches at widest point and then tapering down to a pointed apex. The overall tepal length being 1.5 to 2.5 inches. 2. Arrangement of tepals: regularly arranged overlapping. 3. Fragrance: none. 4. Color: upper surface is bluish purple (PANTONE® #2572C) with reddish bar (PANTONE® #225C) lower surface is bluish purple (PANTONE® #2645U) middle is white with prominent veins.

III. Reproductive organs:

*A. Stamens, filaments and anthers.*—1. Arrangement: irregularly arranged. 2. Stamens: typical and observed 40 to 50 per bloom, length 0.5 inch. 3. Anthers: length ¼ inch (PANTONE® #235U) reddish black. 4. Filament: white with reddish pink hue (PANTONE®#204U).

*B. Pollen.*—1. Color: white. 2. Amount: scarce.

*C. Styles.*—White, even, average length.

*D. Stigmas.*—1. Color: white.

*E. Seed, typical and observed.*—1. Diameter: ⅛ inch. 2. Thickness: 1.16 inch. 3. Color: (PANTONE® #456U) greenish brown. 4. Shape: round. 5. Quantity per bloom: 20 to 30. 6. Description: ¾ inch long persistent style which is clothed with silky white hairs.

I claim:

1. A new and distinct variety of *clematis* plant named 'Festival' as shown and described herein.

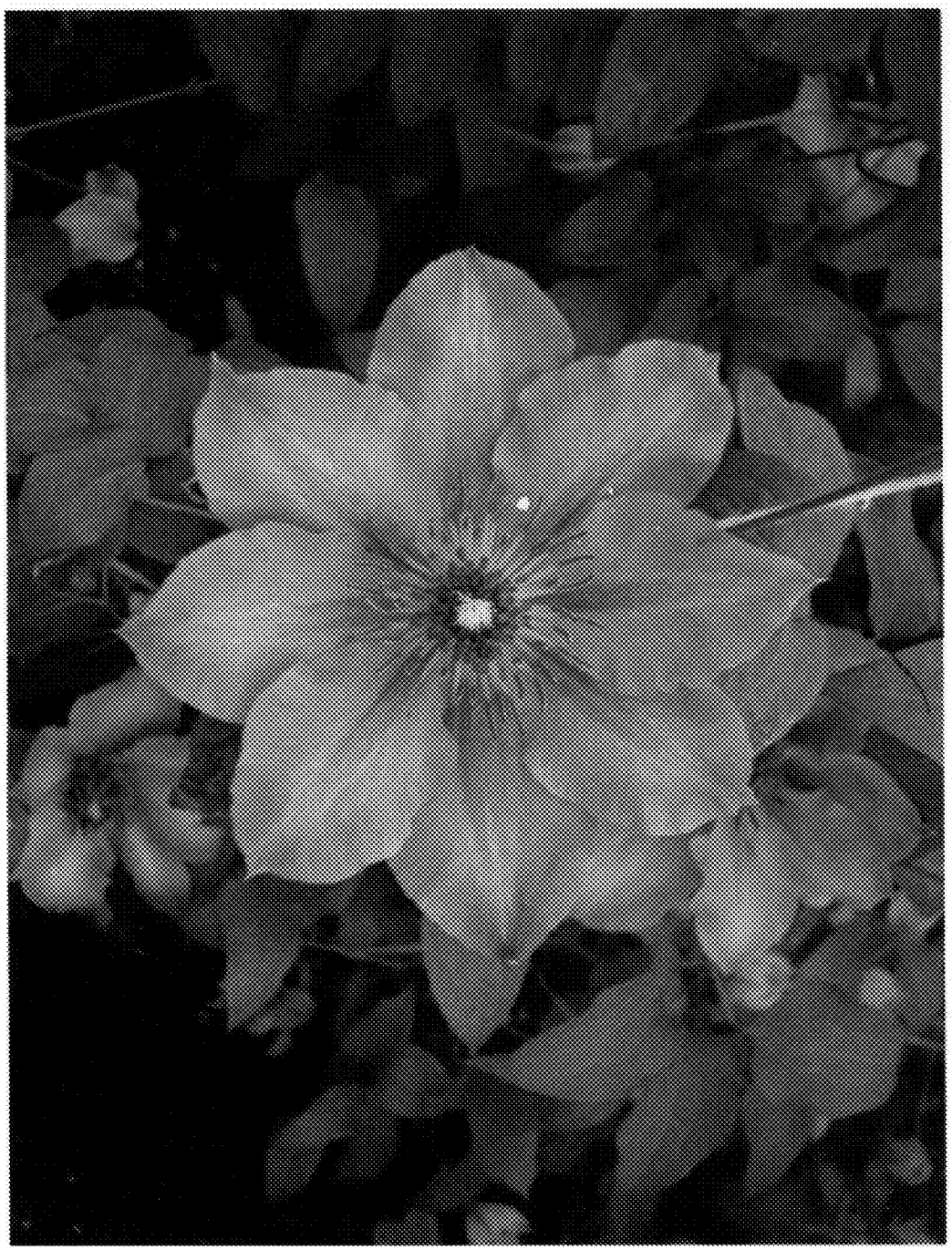

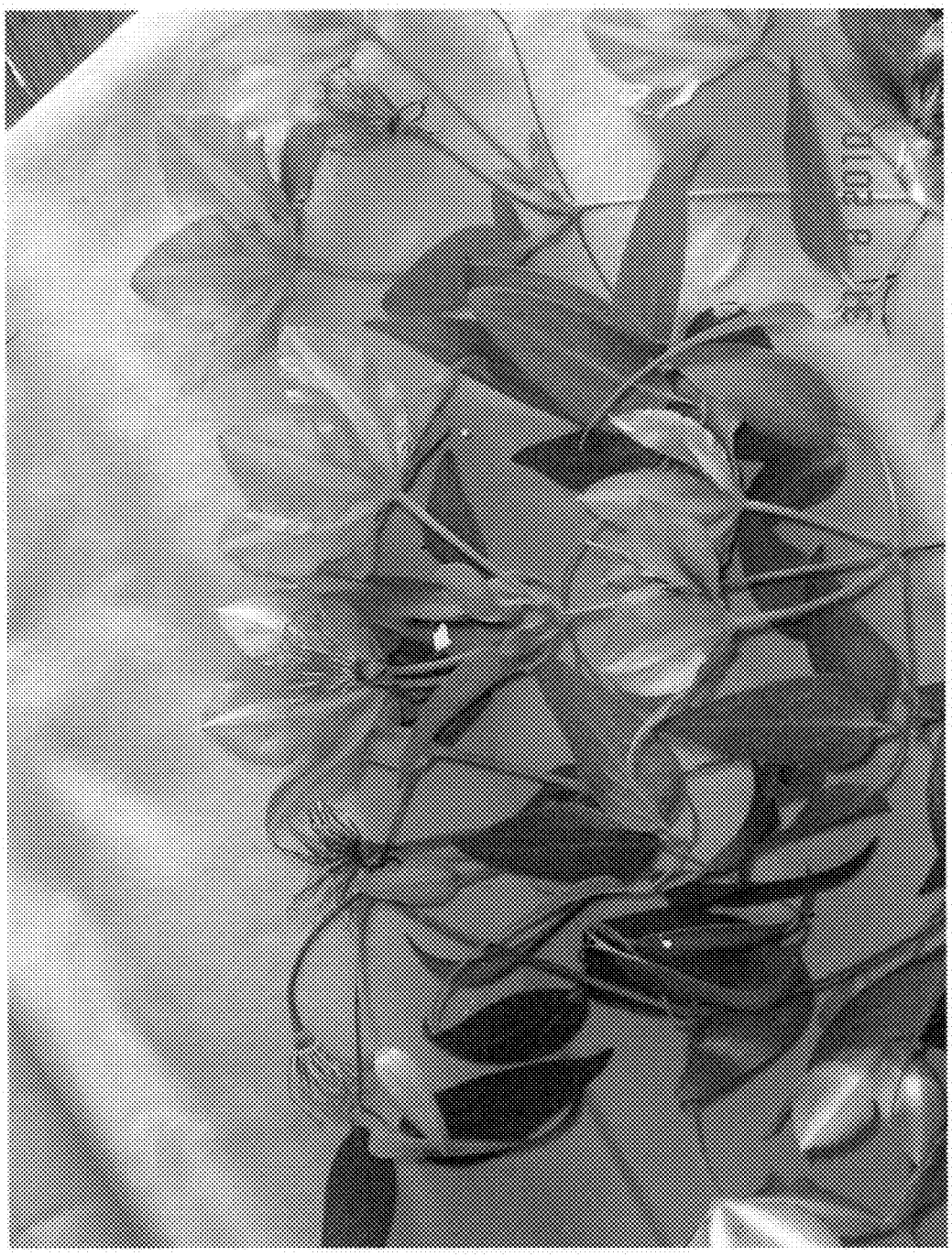

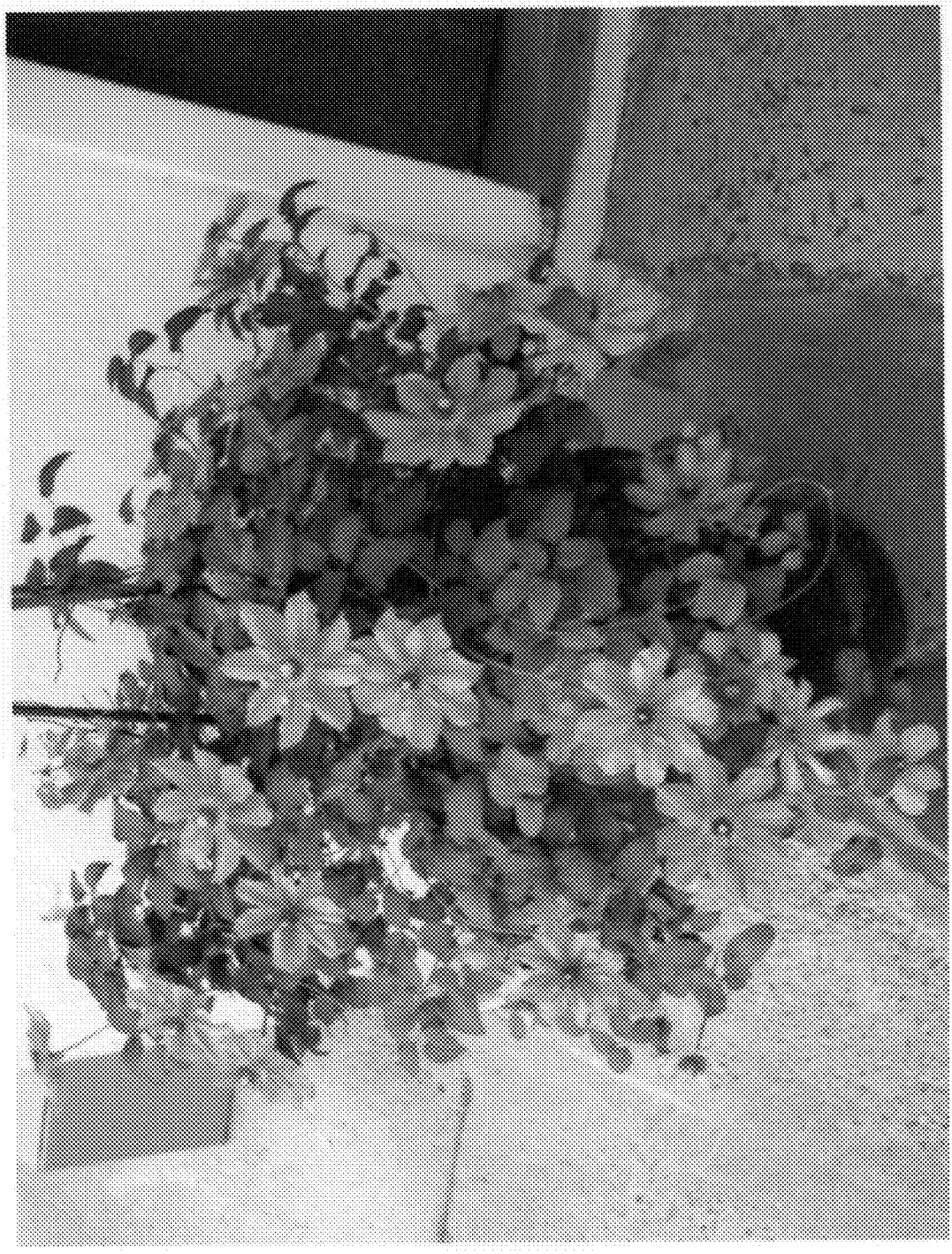

* * * * *